United States Patent
Kramer

(10) Patent No.: US 9,476,828 B2
(45) Date of Patent: Oct. 25, 2016

(54) OPTOELECTRONIC SENSOR FOR TESTING TRANSMISSIVITY OF A FRONT SCREEN

(71) Applicant: SICK AG, Waldkirch (DE)

(72) Inventor: Joachim Kramer, Waldkirch (DE)

(73) Assignee: SICK AG, Waldkirch (DE)

( * ) Notice: Subject to any disclaimer, the term of this patent is extended or adjusted under 35 U.S.C. 154(b) by 141 days.

(21) Appl. No.: 13/847,833

(22) Filed: Mar. 20, 2013

(65) Prior Publication Data

US 2013/0250302 A1  Sep. 26, 2013

(51) Int. Cl.
*G01N 21/00* (2006.01)
*G01N 21/59* (2006.01)
*G01S 17/42* (2006.01)
*G01S 7/481* (2006.01)
*G01S 7/497* (2006.01)
*G02B 26/10* (2006.01)

(52) U.S. Cl.
CPC ............. *G01N 21/59* (2013.01); *G01S 7/4817* (2013.01); *G01S 7/497* (2013.01); *G01S 17/42* (2013.01); *G01S 2007/4975* (2013.01); *G02B 26/10* (2013.01)

(58) Field of Classification Search
CPC ............. G01C 3/08; H01J 3/14; B08B 7/04; H01L 33/00; H01L 21/00; G01N 21/59; G01N 21/00; G03B 21/00
USPC ....... 356/434, 5.01; 250/234; 134/1; 257/98; 91/434, 5.01
See application file for complete search history.

(56) References Cited

U.S. PATENT DOCUMENTS

| 6,468,356 | B1 * | 10/2002 | Crema et al. ..................... 134/1 |
| 2004/0169827 | A1 * | 9/2004 | Kubo ..................... G03B 27/42 353/94 |
| 2005/0006573 | A1 * | 1/2005 | Dollmann et al. ............ 250/234 |
| 2007/0241357 | A1 * | 10/2007 | Yan .................................. 257/98 |
| 2011/0221889 | A1 * | 9/2011 | Knox ..................... G01N 21/53 348/135 |
| 2013/0003041 | A1 * | 1/2013 | Sigmund et al. ............ 356/5.01 |

FOREIGN PATENT DOCUMENTS

| DE | 43 40 756 A1 | 6/1994 |
| DE | 100 25 511 C1 | 12/2001 |
| DE | 103 60 950 A1 | 7/2005 |
| DE | 10 2008 032 216 A1 | 1/2010 |
| EP | 2 237 065 A1 | 10/2010 |
| EP | 2 447 733 A1 | 5/2012 |

OTHER PUBLICATIONS

Office Action of German Patent Office in Application No. 10 2012 102 395.6.
European Patent Office, European Search Report, Application No. EP 13 15 7763, dated Jul. 2, 2013, four (4) pages.

* cited by examiner

*Primary Examiner* — Tarifur Chowdhury
*Assistant Examiner* — Jamil Ahmed
(74) *Attorney, Agent, or Firm* — Nath, Goldberg & Meyer; Jerald L. Meyer

(57) ABSTRACT

An optoelectronic sensor (10) has a circumferential front screen (42) comprising a curvature both in a circumferential direction and in a transverse height, thus focusing light reflected at the inside of the front screen (42). Test light passes from a test light transmitter (50*a-f*) through the front screen (42) to a reflector (52*a-f*) and subsequently onto a test light receiver (56*a-b*). A decreasing light transmissivity of the front screen (42) is detected based on a decrease of a signal generated by the test light in the test light receiver (56*a-b*). The test light receiver (56*a-b*) is arranged on a same side of the front screen (42) as the reflector (52*a-f*) such that the test light path (54*a-f*) leads from the reflector (52*a-f*) via reflection on the inside of the front screen (42) to the test light receiver (56*a-b*).

19 Claims, 6 Drawing Sheets

Figure 1:
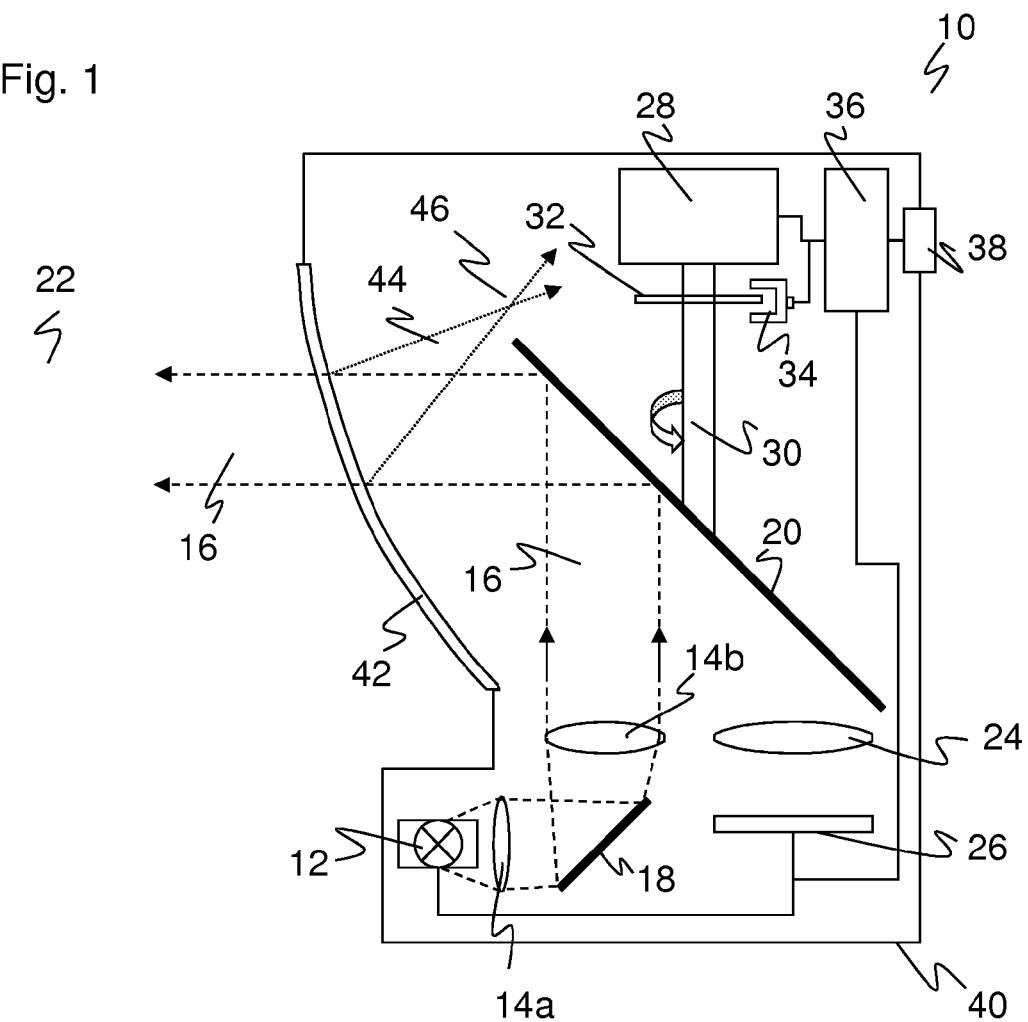

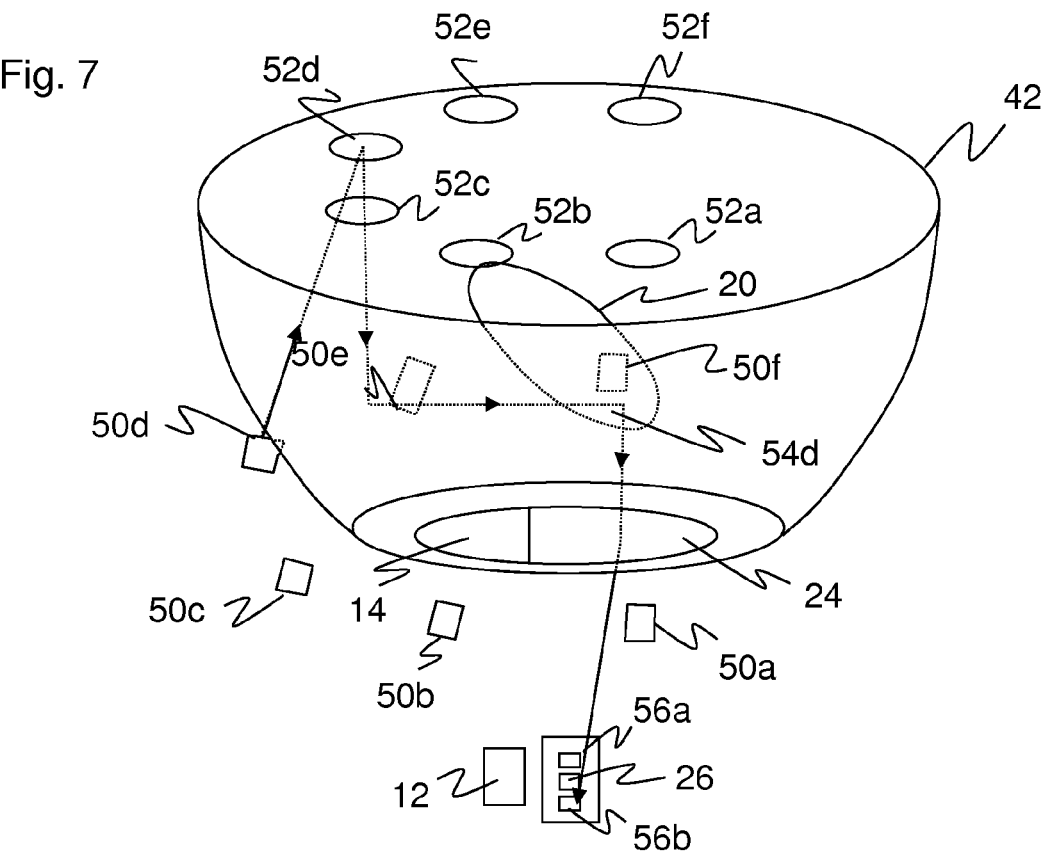
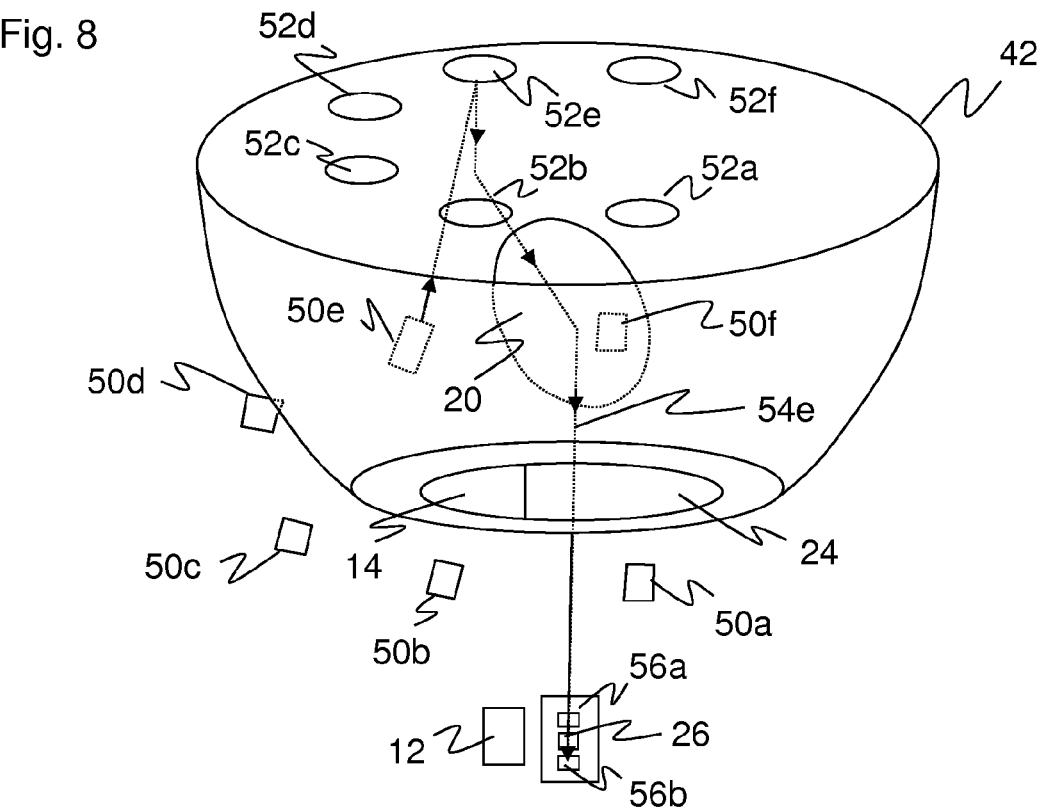

OPTOELECTRONIC SENSOR FOR TESTING TRANSMISSIVITY OF A FRONT SCREEN

The invention relates to an optoelectronic sensor with a circumferential front screen and a method for testing a light transmissivity of a front screen of a sensor.

Laser scanners are used in many applications for object detection. A light beam generated by a laser sweeps periodically over a monitoring plane by means of a deflection unit. Normally, a rotating mirror is used as the deflection unit, which scans a field of view of up to 360° in discrete angular steps within a fixed plane. The transmission light is remitted by objects in the monitoring plane and evaluated in the scanner. The angular position of the object is determined from the angular position of the deflecting unit, and additionally the distance of the object from the laser scanner is determined from the light time of flight and using the speed of light. In case of the monitoring area being a scanning plane, all possible object positions are detected with these polar coordinates in two dimensions. Two basic principles for the determination of the light time of flight are known. Phase-based methods modulate the continuous transmission light and evaluate the phase between the transmitted and the received light. In pulse-based methods, the laser scanner measures the time of flight until a transmitted light pulse is received again.

In safety technology, laser scanners are used for monitoring a source of danger, such as a dangerous machine. One such safety laser scanner is known from DE 43 40 756 A1. There, a protected field is monitored that is no to be entered by personnel during operation of the machine. If the laser scanner detects a forbidden intrusion into the protected field, such as a leg of an operator, it triggers an emergency stop or shut-down of the machine. Other intrusions into the protected field, for example by static parts of machines, may previously be taught as admissible. Often, warning fields are defined in front of the protected fields, where intrusions at first trigger only a warning in order to prevent the intrusion into the protected field and the resulting safeguarding in time and to increase the availability of the machine.

Sensors used in safety technology must work particularly reliable and therefore meet strong safety requirements, for example the EN13849 standard for machine safety and the device standard EN61496 for contactless protective devices. To satisfy these safety standards, a number of measures have to be taken, like a safe electronic evaluation by redundant or diversified electronics, testing and monitoring of functions or in particular monitoring the contamination of optical components, such as a front screen, and/or providing test targets of a defined remission that have to be detected at corresponding scanning angles.

As a protection against environmental influences, laser scanners are usually equipped with a front screen which is part of the housing and transmissible for the scanning beams. Two aspects have to be considered so that the front screen does not affect the optical measurement.

Firstly, because the front screen forms two optical boundary surfaces, a reflection of the transmission beam is generated which can interfere with the measurement. The conventional optical construction of a laser scanner is a coaxial arrangement of transmission and reception beam paths. In order to prevent the front screen reflection from impinging on the receiver, the front screen is tilted. Thereby the front screen reflection is deflected upwardly and fades in an optical trap. The description of a tilted front screen refers to a sectional view in a fixed angular position of the deflection unit. In order to present a tilted surface in every position of the rotational movement, the front screen forms a corresponding body of revolution, i.e. a frustum of a cone. The defined deflection of the front screen reflection into an optical trap with such a shape of the front screen requires the transmission beam to always impinge at a same height. If this condition is not met, however, either a lot of space is required for an extended optical trap, or scattered light of the front screen reflection can get into the reception path after all.

Secondly, for a functional correct and safe operation it has to be continually monitored according to the standards mentioned above whether the front screen comprises scratches, dust, or any other abnormality. This is usually done by a contamination measurement in which a test light beam passes through the front screen. When used in an environment with environmental conditions such as fog or extreme temperatures, in particular outdoors, but also in the vicinity of corresponding processes indoors, a fogging can additionally be formed on the outside of the front screen. This may also lead to a deterioration of the image of the reception light spot generated by the scan beam and thus to a dangerous failure. Since the fogging cannot be reliably detected by a conventional transmission measurement, it is usually prevented by heating the front screen.

In a laser scanner with a frusto-conical front screen according to the prior art, the transmission measurement is done by passing through the front screen at several locations with a pair of a test light transmitter and an associated test light receiver each. The test light transmitter may be arranged outside and the test light receiver inside the front screen, so that the front screen is located directly on the common line of sight. It is also known to use a reflector and to arrange both test light transmitter and test light receiver on the same side with respect to the front screen. Then, the front screen is passed through by the test light twice. In a further alternative, a reflector and a test light receiver are inside the sensor, so that the front screen again is passed through only once.

In order to detect conditions such as temperature or aging of the test light transmitters and test light receivers, reference paths are provided on which the test light does not pass through the front screen. In a known embodiment, seven test light paths and two reference paths are required to obtain sufficient information about the front screen for example in a relevant angular range of 270°. Thus, a total of 9 LEDs, 9 photodiodes, and a circuit board for the evaluation are needed, which contribute to space requirements and manufacturing costs accordingly.

From EP 2 447 733 A1, a laser scanner with a special shape of the front screen is known. The front screen has focusing properties due to its curvature so that the front screen reflection is deflected into a focus area irrespective of the height where the transmission beam impinges. However, EP 2 447 733 A1 does not contribute new aspects to the monitoring of transmissivity properties of the front screen.

It is therefore an object of the invention to reduce the effort of the monitoring of the front screen.

This object is satisfied by an optoelectronic sensor having a circumferential front screen comprising a curvature both in a circumferential direction and in a height direction transverse to the circumferential direction and thus having a circumferential focus area in which light reflected at the inside of the circumferential front screen is focused, wherein at least one test light transmitter, at least one reflector, and at least one test light receiver form a test light path on which test light passes from the test light transmitter through the front screen to the reflector and subsequently onto the test light receiver, and wherein an evaluation unit is provided which is configured to detect a decreasing light transmissivity of the front screen based on a decrease of a signal generated by the test light in the test light receiver, wherein the test light receiver is arranged on a same side of the front screen as the reflector such that the test light path leads from the reflector via a reflection on the inside of the front screen to the test light receiver.

The object is also satisfied by a method for testing a light transmissivity of a circumferential front screen of an optoelectronic sensor, wherein test light passes on a test light path from at least one test light transmitter through the front screen to at least one corresponding reflector and subsequently onto a test light receiver, and wherein a decreasing light transmissivity of the front screen is detected from a decrease of a signal generated in the test light receiver by the test light, wherein the test light is partially reflected at an inside of the front screen after reflection at the reflector and is at the same time focused due to a curvature of the front screen both in a circumferential direction and a height direction transverse to the circumferential direction, wherein the test light is subsequently detected on the same side of the front screen as the reflector in the test light receiver.

The invention starts from the basic idea to utilize the focusing or imaging properties, respectively, of the boundary surfaces of a special curvedly formed front screen of an optoelectronic sensor for a simplified contamination measurement. This front screen has a curvature both in a circumferential direction and transverse thereto in a height direction and thus a focus area in which light impinging on the inside of the front screen is partially focused by reflection. Strictly speaking, the light is reflected twice at the inside of the front screen, namely, on both boundary surfaces once upon entry into the material of the front screen and again upon exit. The circumferential front screen with these curvature properties and the associated focus area may encompass the full 360° range or only a certain angular portion thereof.

A test light transmitter, a reflector, and a test light receiver in this order form a test light path, and test light detected in the test light receiver is monitored for a drop indicative of a reduction in light transmissivity of the front screen which cannot be tolerated. Test light receiver and reflector are arranged at a same side of the front screen so that the test light path from the reflector via a reflection at the inside of the front screen leads to the test light receiver. The inside of the front screen with its imaging properties arising from the curvature is therefore used for the test light path. It is also possible that a test light transmitter, a reflector, and a test light receiver, respectively, are arranged above or below the front screen. Hence, "at a same side" also describes a region of space which may be defined by an extension of the front screen. It is only important that the test light path passes through the front screen at least once, for example by the test light sender being arranged outside the front screen and test light receiver and reflector being arranged inside the front screen. Since a point measurement with only one test light path usually is not sufficient to evaluate the contamination of the entire front screen, a plurality of test light transmitters is often provided. As explained in the following, by utilizing the curvature properties of the front screen, the number of test light receivers does not need to be increased, or at least does not need to be increased to the same degree.

The invention has the advantage that the manufacturing costs and the space required for the contamination measurement are significantly reduced. It is still detected whether the front screen enables a safe operation of the sensor reliably and in conformity with the standards.

The sensor preferably is configured as a laser scanner comprising a light transmitter for transmitting a transmission light beam into a monitoring area, in particular a monitoring plane, a light receiver for generating a reception signal from a remitted light beam remitted from objects in the monitoring area and a deflection unit rotatable around a rotational axis for periodically deflecting the transmission light beam in order to scan the monitoring area in the course of the rotation, wherein the evaluation unit is further configured to obtain information about objects in the monitoring area from the reception signal. Here and in the following, a preferred feature refers to a feature that is advantageous, but completely optional. The monitoring plane is also called scanning plane or scan plane. In case of a rotating deflection unit, the monitoring plane is perpendicular to the axis of rotation. It is also possible to cyclically tilt the sensor with respect to the axis of rotation. Then, a three-dimensional space region is monitored instead of a plane, which geometrically is the complement of a double cone. Such a space region may also be referred to as a monitoring plane as a simplification within the framework of this description, and a perpendicular orientation to this space region refers to a central plane. The remitted light beam is usually lad via the same deflection unit as the transmitted light beam. Often, a particular region of the deflection unit is used for deflecting the transmission beam, and the remainder of the deflection unit is used for deflecting the remitted light to the light receiver. In principle, it is also possible to use a separate deflector each.

The test light receiver is preferably arranged near the rotational axis and with its optical axis parallel thereto so that the test light path passes from the inside of the front screen via the deflection unit to the test light receiver. The deflection unit thus always faces the reflector and test light transmitter, respectively, currently to be tested. As a consequence, for a plurality of test light paths their rear parts after the deflection unit have a particularly compact arrangement.

The evaluation unit preferably is configured to activate the test light transmitter synchronized with the rotation. As a test light path leading via the deflection unit is only complete at a correct orientation of the deflection unit, it is thus ensured that only the respective matching test light transmitter is active, and vice versa, that the test light of an active test light transmitter has a complete test light path. As an alternative to synchronizing, the test light transmitters may also be activated with any other timing, where the orientation of the deflection unit decides whether test light arrives at the test light receiver.

Reception optics are preferably arranged in front of the light receiver, wherein the reception optics are also part of the test light path between deflection unit and test light receiver. Such receiving optics are anyway required by the sensor in virtually all embodiments. Due to the test light beam paths according to the invention, these reception optics may also be used for the test light paths.

The reflector preferably is arranged near the focus area of the front screen with an offset to the focus area. The arrangement in the vicinity of the focus area ensures that the test light arrives near a known position at the end of the test light path, preferably in the center of the sensor or where light transmitter and light receiver of the sensor are. At the same time, when the offset is provided, test light does not impinge on the light receiver where, without additional preventive measures, it affects the measurement as interfering light with respect to the actual signal of the sensor.

The sensor preferably comprises a plurality of reflectors which are arranged in a circumferential distribution in a plane parallel to the monitoring plane, wherein each reflector has an offset to the focus area and a differing angle offset relative to a radial direction to the focus area so that the test light reflected by the plurality of reflectors is guided via the front screen to a common test light receiver. A plurality of test light transmitters corresponding to the plurality of reflectors is preferably provided to form a plurality of test light paths. However, due to this particular arrangement of the reflectors, it is not necessary to also provide a corresponding number of test light receivers. As a result, components can be saved, and the front screen be tested at more intersection points than the number of test light receivers. In particular, it is possible to arrange the reflectors such that all test light paths end in one and the same test light receiver, or to form two groups whose test light paths end in one respective common test light receiver and thus overall in only two test light receivers.

The test light transmitter preferably comprises test light transmission optics, wherein the test light transmission optics are integrally formed with a socket of the front screen. By means of test light transmission optics, collimated or otherwise beam shaped test light beams are generated, for example by an aperture. The region on the front screen where the beam passes and thus the contamination monitoring can thus further be optimized. By integral forming with a socket of the front screen, manufacturing and adjustment of such test light transmission optics is particularly easy. For example, lenses may be molded into the socket.

A plurality of test light receivers is preferably arranged on a same circuit board. Due to the design of the light paths according to the invention, other than in the prior art, test light receivers can be arranged in very close proximity. This enables a space and cost saving common circuit board of some or even all test light receivers. This may even be the circuit board of the sensors light receiver, so that no additional circuit board is required for the light transmissivity test.

The light transmitter and the test light transmitters are preferably configured to transmit light with distinguishable modulation properties or spectral properties. In case that the arrangement of the test light paths and other measures are insufficient to prevent, or even systematically cause, that test light arrives at the light receiver, it can be distinguished from the actual measurement signal based on the distinguishable properties. That way, interfering effects of the test light are suppressed in the measurement signal.

The reflector preferably is selective for test light and is arranged in the focus area, wherein the light receiver is also configured as a test light receiver. In this embodiment, test light is even systematically caused to impinge on the light receiver. The selective reflection prevents that stray light of the light transmitter impinges on the light receiver via the test light paths. In this arrangement, test light receivers are replaced by a dual function of the light receiver, where in the limiting case no separate test light receiver is required in the first place.

At least one reference light transmitter is preferably arranged so that its reference test light impinges on a corresponding reflector without passing through the front screen. The reference light transmitter is preferably identical to the test light transmitter, and its light path is substantially the same with the difference that it does not pass through the front screen. Thus, the reference test light is unaffected by interferences of the front screen and can be used to compensate other effects such as temperature or aging. Analogously to the test light paths, the reflector of the reference light transmitter can also be arranged with a suitable offset from the focus area so that the reference test light impinges on a test light receiver together with test light of at least one test light transmitter. This not only has the advantage that a separate reference light receiver can be saved, but it is also a more accurate reference, namely, directly the test light receiver to be tested rather than merely an identical test light receiver.

At least one fogging test receiver is preferably arranged in the focus area, wherein the evaluation unit is configured to detect a fogging of the front screen from a decrease of a part of a transmission light beam of the sensor which is reflected into the fogging test receiver by the front screen. Fogging is formed by humid air and changes in temperature and thus mainly outdoors. This embodiment also relates to an impairment of light transmissivity of the front screen. However, it is tested in a completely different way than in the other embodiments. No test light transmitters, reflectors, and test light receivers, and no corresponding evaluation is required. Instead, the front screen reflection of the light transmitter is measured by the fogging test receiver.

The sensor is preferably configured as a distance-measuring laser scanner in that the light time of flight between transmission and reception of the light beam and from that the distance of an object can be determined in the evaluation unit, wherein an angle encoder for detecting the angular position of the deflection unit is provided so that for detected objects in the monitoring plane two-dimensional polar coordinates are available. This enables a complete position detection within the monitoring plane. In addition, object contours can be measured if required.

The sensor is preferably configured as a safety laser scanner with a safety output by the evaluation unit being configured to determine whether an object is present in a protected area within the monitoring plane and to thereupon output a safety-related shut-down signal via the safety output. In applications in safety technology, excluding interference of the front screen is of particular importance because health and life of persons depend on the reliable operation.

The test light paths exploit the curvature properties of the front screen. Instead of a frustum of a cone, the front screen is preferably designed as a free-form surface. A curvature, in particular a convex curvature, is not only provided in a circumferential direction, but also perpendicular thereto in a height direction. This curvature also serves to guide a front screen reflection from transmission light emerging from the sensor into the focus area irrespective of the height where the transmission light impinges on the front screen. Therefore the light paths of the front screen reflection and the test light are mostly identical with reverse direction. This is further supported when a transmission lens and a reception lens of the sensor have similar focal lengths.

The front screen preferably forms a body of revolution with respect to a central axis perpendicular to the monitoring plane, wherein the central axis in particular is a rotational axis of the deflection unit. Such a body of revolution is not necessarily also rotationally symmetrical, since instead of a 360° field of view also smaller fields of view of for example 270°, 180° or other angular ranges are possible. In that case, there are angular regions where the sensor comprises dead zones which can be used for mounting on a wall, internal wiring or electronic, or a test target for testing the light transmitter.

The direction perpendicular to the monitoring plane may be referred to as height direction for simpler language. The curvature of the front screen preferably increases or decreases monotonically with the height. This also includes a continuous curvature in height direction. On the other hand, planar intermediate regions or facets are also conceivable which correspond to a discrete approximation of a continuous curvature by polygonal surfaces. More preferably, the curvature is strictly monotonic, thus avoiding spherical portions. A particularly advantageous curvature results in a front screen curved like a bell or a goblet.

Advantageously, each secant passing through a section of the front screen perpendicular to the monitoring plane runs tilted to the monitoring plane. This in particular includes the secant passing through the upper and lower edge of the front screen. The curved contour of the front screen as a whole is thus tilted with respect to a line perpendicular to the monitoring plane. The front screen is not perpendicular to the transmission beam at any point so that the front screen reflection is always deflected upwards or downwards from the beam path. This can also be expressed, as an alternative to a definition based on secants, that the largest possible body having no curvature in height direction which is inscribed into the curved front screen is a frustum of a cone with tilted walls rather than a circular cylinder with perpendicular walls.

The front screen preferably has the shape of a concave mirror which deflects reflections of the transmitted light beam at the front screen irrespective of a height position with respect to the monitoring plane into the circumferential focus area. Only when considering a fixed angular position there is a real focal point. By the varying angular positions, a ring of focal points is formed which is referred to as the circumferential focus area. The circumferential focus area is preferably arranged above or below the front screen, at least above or below the light beams of light transmitter and light receiver of the sensor. This avoids interference.

The front screen preferably comprises a portion of a parabola, a hyperbola, an ellipse, or an aspheric surface in a section perpendicular to the monitoring plane. These are specific embodiments of the curvature with the desired focusing properties. In three dimensions, this leads to a portion of a rotational paraboloid, hyperboloid, or ellipsoid in case of a front screen formed as a body of revolution. The portion may be both axial and off-axial, i.e. may include or exclude characteristic points such as vertices, focal points, and the like.

The sensor preferably comprises an optical trap to at least partially absorb reflections of the transmitted light beam at the front screen. The optical trap more preferably is designed as a body of revolution and arranged in the focus area. Thus a small extent of the optical trap suffices to capture the front screen reflections irrespective of the height position and the angular position of the transmission beam. The body of revolution preferably extends over the same angular range as the front screen. The optical trap is thus effective everywhere in circumferential direction of the front screen over the entire field of view of the sensor. The optical trap may be formed for example as an aperture with an opening in the focus area and having a cavity. The trap thus specifically captures the light of the front screen with its aperture. Inside, the optical trap preferably comprises light absorbing and/or light distributing material so that the light cannot leave the optical trap, or that only a small part can leave. Suitable materials, for example, are a black coating, black velvet, or anodized aluminium.

Light transmitter and light receiver are preferably not arranged coaxially with each other. For example, the optical axis of the light receiver is substantially the rotational axis of the deflection unit, and the optical axis of the light transmitter has a parallel offset. Such an arrangement results in an up and down movement of the transmission beam, because the transmission beam does not centrally impinge on the deflection unit so that there is a height offset in dependence on the angular position. Due to the curvature of the front screen, the front screen reflection is nevertheless deflected reliably and in a defined direction so that it for example may be absorbed in an optical trap. At the same time, the non-coaxial arrangement is advantageous because it enables a compact construction of the sensor which in particular allows for a transmission and reception unit with optimized height. The setting or adjustment of the signal dynamics is also facilitated, in particular in a near zone, while simple optical elements may be used.

The method in accordance with the invention can be further developed in a similar manner with additional features and shows similar advantages. Such advantageous features are described in an exemplary, but not exclusive manner in the subordinate claims following the independent claims.

Figure 2:
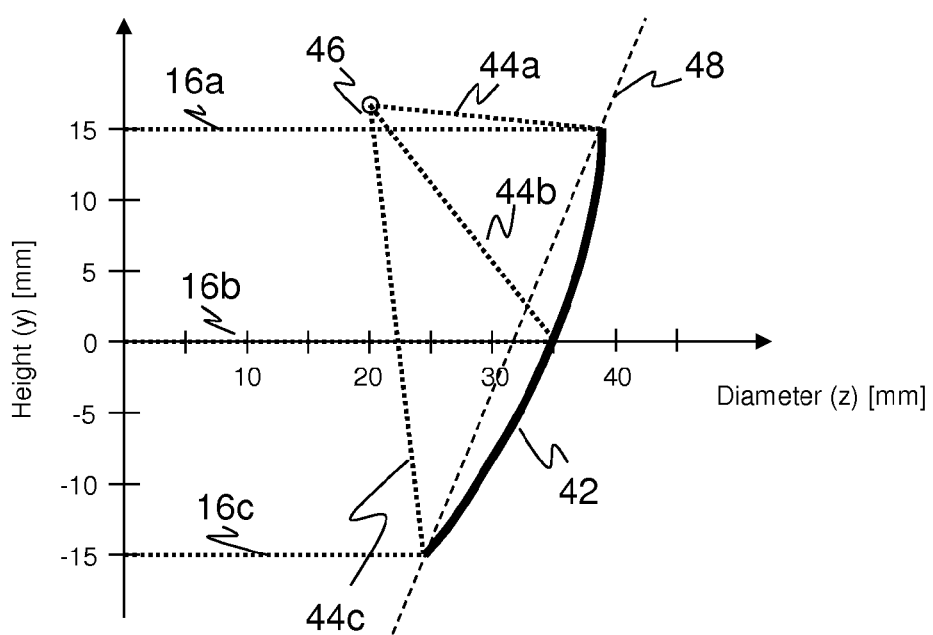
Figure 3:
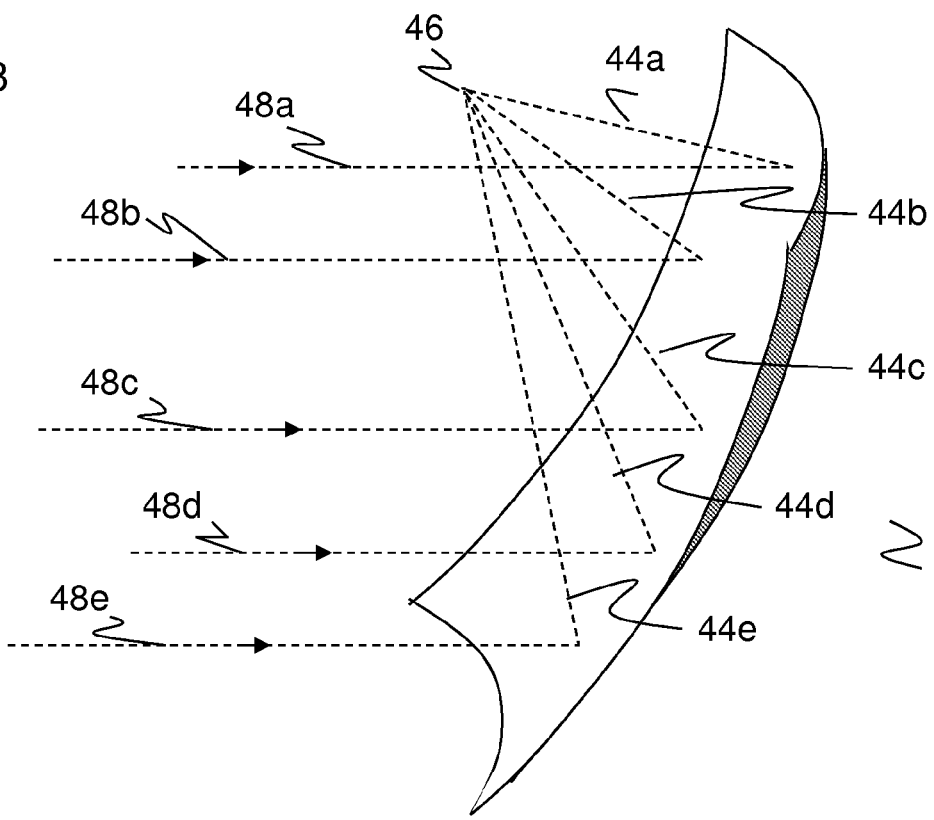
Figure 4:
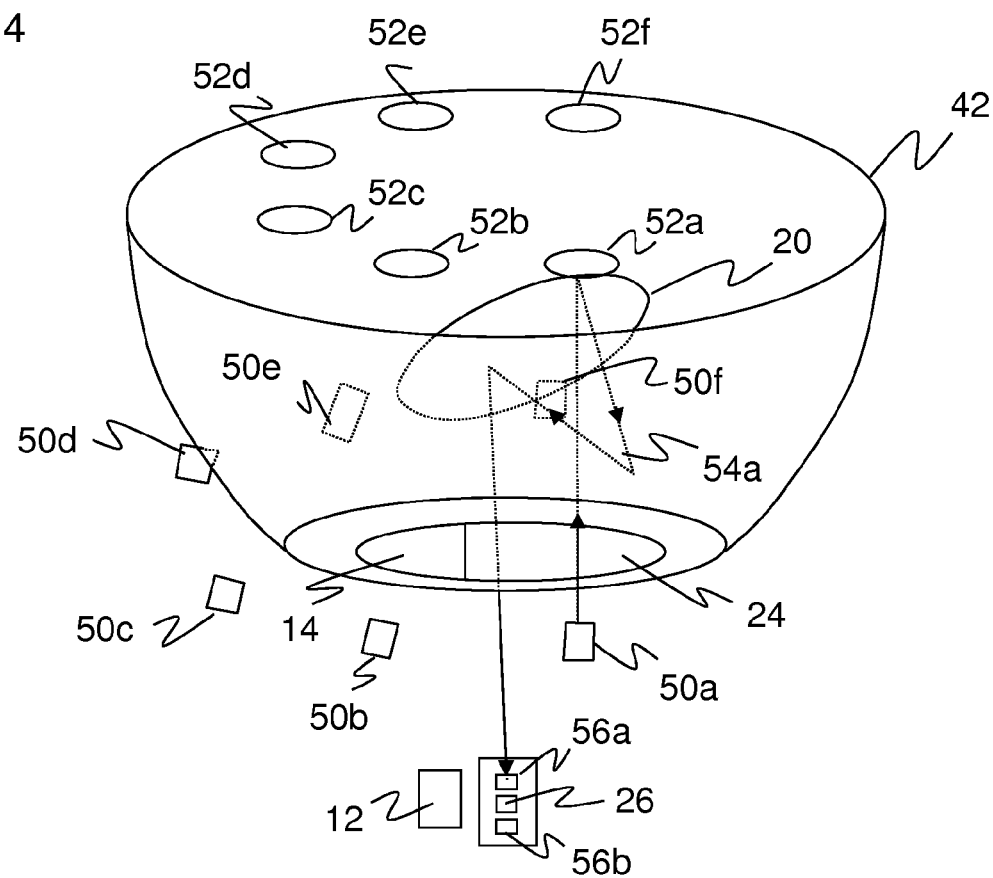
Figure 5:
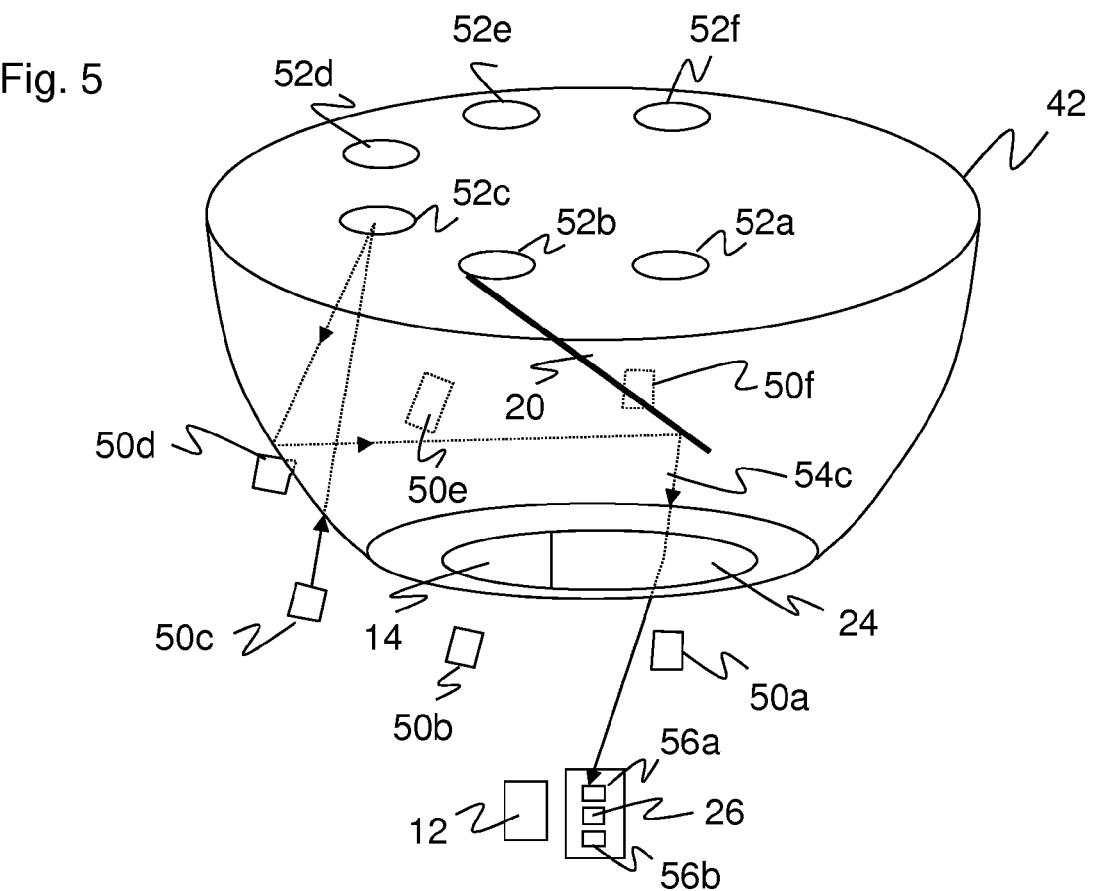
Figure 6:
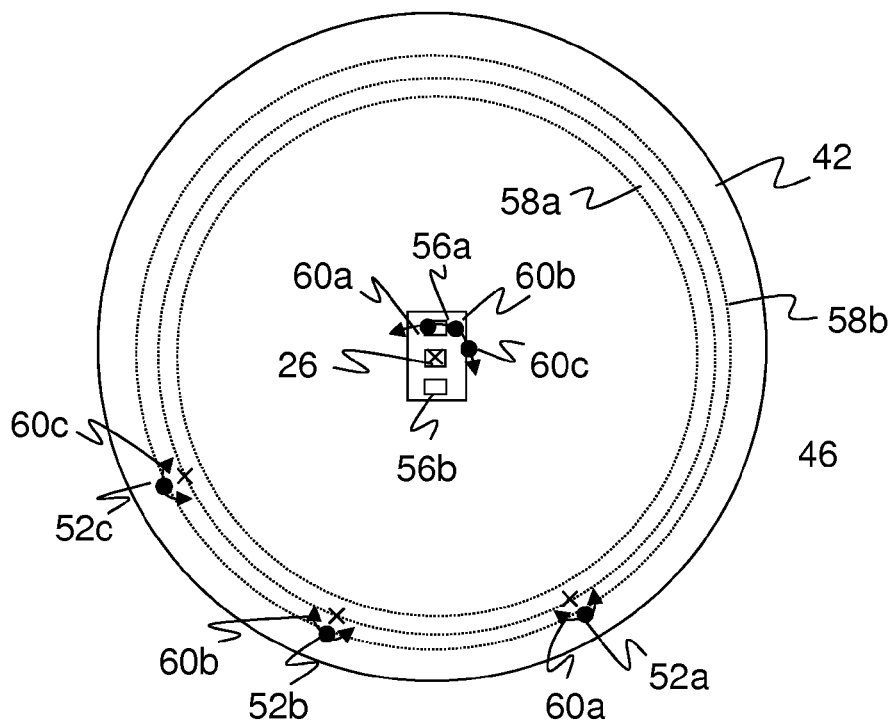
Figure 9:
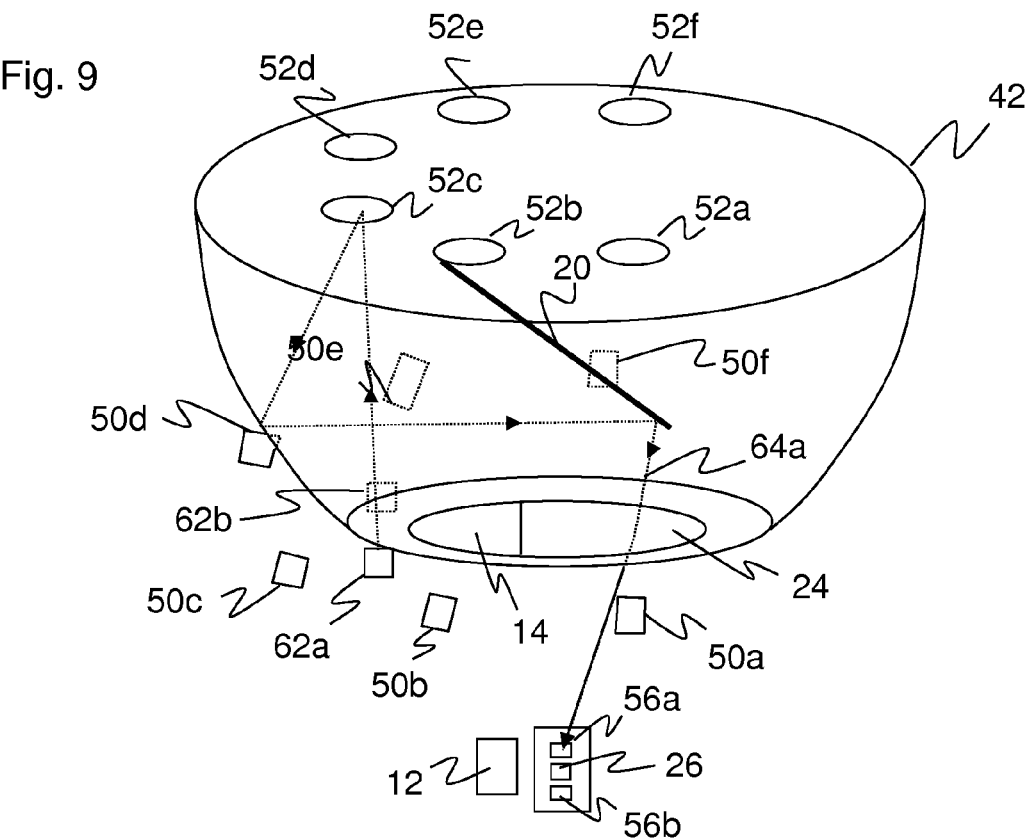
Figure 10:
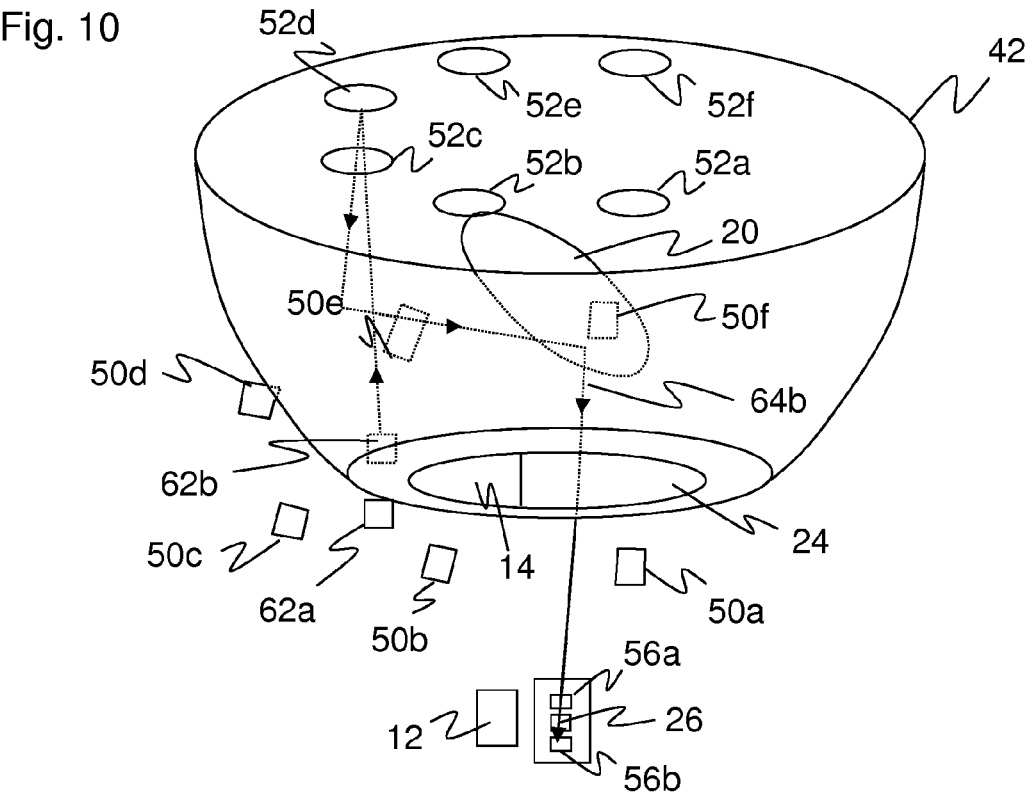
Figure 11:
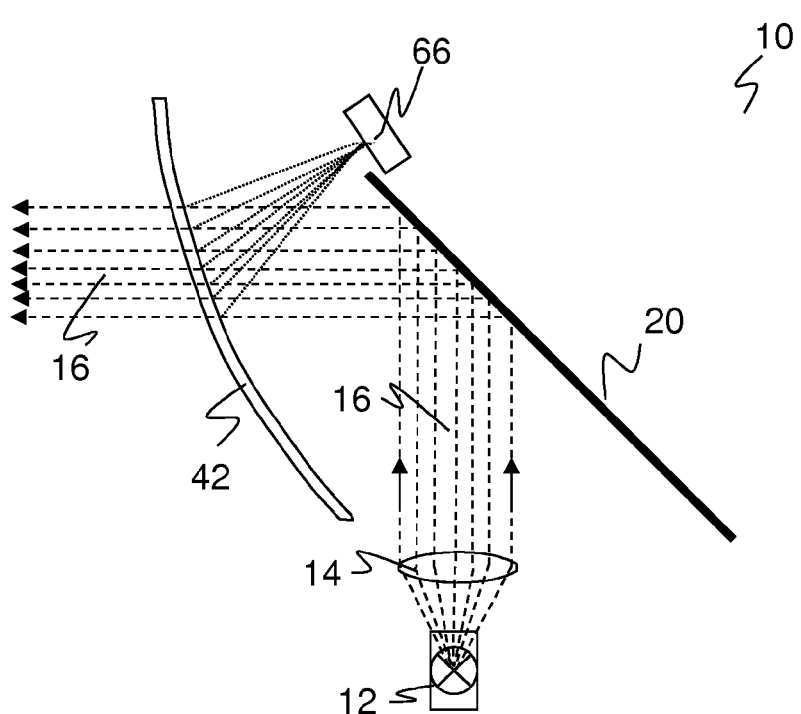

The invention will be explained in the following also with respect to further advantages and features with reference to exemplary embodiments and the enclosed drawing. The Figures of the drawing show in:

FIG. 1 a schematic cross sectional view of a laser scanner with a front screen having a curvature in two dimensions;

FIG. 2 a section through an embodiment of the front screen of the laser scanner according to FIG. 1 perpendicular to its monitoring plane;

FIG. 3 a three-dimensional view of an embodiment of the front screen of the laser scanner according to FIG. 1;

FIG. 4 a three-dimensional view of a front screen and the elements of the test light paths as well as the beam path of the first test light path;

FIG. 5 a three-dimensional view of the front screen according to FIG. 4 with the beam path of a third test light path;

FIG. 6 a plan view of the front screen according to FIG. 4 to illustrate the arrangement of the reflectors and the beam path of the test light caused thereby;

FIG. 7 a three-dimensional view of the front screen according to FIG. 4 with the beam path of a fourth test light path;

FIG. 8 a three-dimensional view of the front screen according to FIG. 4 with the beam path of a fifth test light path;

FIG. 9 a three-dimensional view of the front screen according to FIG. 4 with the beam path of a first reference light path;

FIG. 10 a three-dimensional view of the front screen according to FIG. 4 with the beam path of a second reference light path;

FIG. 11 a simplified sectional view through the laser scanner according to FIG. 1 and the beam path of a front screen reflex to illustrate a fogging measurement based on the front screen reflection.

FIG. 1 shows a schematic cross section through an optoelectronic sensor 10 in an embodiment as a laser scanner. A light transmitter 12, for example having a laser light source, generates a transmission light beam 16 with individual short light pulses with help of transmission optics 14a, 14b. As an alternative, the sensor 10 operates with a phase method instead of a pulse method, as described in the introduction. The transmission light beam 16 is, by means of a deflecting mirror 18 and a deflection unit 20, transmitted into a monitoring area 22. Instead of a deflecting mirror 18, a polarization filter may also be used. Generally, the coupling of the transmission light beam 16 into the transmission light path via the deflection unit 20 can be done in any alternative known manner, for example with only one transmission optics or on a direct light path without deflecting mirror 18.

The transmission light beam 16 is remitted in the monitoring plane 22 by objects possibly being present therein, and at least partially returns to the sensor 10 as a remitted light beam which is attenuated and/or scattered depending on the optical properties of the object surface. The remitted light beam again impinges on the deflection unit 20 and is guided onto a light receiver 26, for example a photodiode, through reception optics 24. As already explained for light transmitter 12 and transmission optics 14, 14b, the design and arrangement of transmission optics 24 as well as the position of the light receiver 26 is to be understood purely as an example. Various alternative embodiments are possible, such as reception optics moving with the deflection unit 20, reception optics comprising several lenses, a beam shaping of the remitted light beam already prior to impinging on the deflection unit 20, and the like.

The deflection unit 20 is configured as a rotating mirror which is continuously rotated by a motor 28. Therefore, the transmission light beam 16 scans a monitoring plane perpendicular to the rotational axis 30 in the course of the rotational movement. In an alternative embodiment, an additional tilting of the rotational axis 30 is conceivable in order to detect a three-dimensional space region as the monitoring area 22. In that case, the monitoring plane refers to the central plane of this space region.

The arrangement of light transmitter 12 and light receiver 26 in this embodiment is not coaxial. Therefore, the transmission light beam 16 does not centrally impinge on the deflection unit 20, but in varying heights in the course of the rotational movement. This results in an up and down movement of the transmitted light beam 16 to an extent depending on the distance between the optical axis of the light transmitter 12 and the rotational axis 30. In an alternative embodiment, light transmitter 12 and light receiver 16 are coaxially arranged, for example by means of a beam splitter, and there is no up and down movement of the transmission light beam 16.

With the sensor 10 as illustrated, a viewing angle of up to 270° can be monitored. In addition to the elements shown, a reference target may be provided in a rear region to test the function of the light transmitter 12. This is one exemplary way of satisfying one of the requirements of the safety standards mentioned in the introduction and making sensor 10 a safe sensor. In principle, the optical design as shown also allows a larger viewing angle of up to 360°.

The respective angular position of the deflection unit 20 is detected by an encoder which for example comprises a code disc 32 and a fork light barrier 34. Alternative methods to measure an angular position are possible. The transmission light beam 16 generated by the light transmitter 12 thus sweeps over the monitoring plane 22 generated by the rotational movement. In case that a remitted light beam from the monitoring plane 22 is received by the light receiver 26, the angular position of the object in the monitoring plane 22 can be determined from the angular position of the deflection unit 20 measured by the encoder 32, 34.

Additionally, the time of flight of the individual laser light pulses from their transmission to the reception after reflection at an object in the monitoring plane 22 is determined. From the light time of flight, the distance of the object from the sensor 10 is determined using the speed of light. This evaluation is done in an evaluation 36 which is connected to the light transmitter 12, the light receiver 26, the motor 28, and the encoder 32, 34. Hence, two-dimensional polar coordinates of the positions of all objects in the monitoring area 20 are available via the angle and the distance.

For applications in safety technology in particular, the goal of the evaluation is to provide a safety signal at a safe output 38 (OSSD, Output Signal Switching Device), for example to trigger an emergency shutdown of a connected machine. In these applications, preferably the other requirements mentioned in the introduction are also observed to satisfy the relevant safety standards. Via the angle and distance data, the evaluation unit 36 determines the position of an object in the monitoring plane 22. This is compared with a two-dimensional protected field whose geometry is stored in a memory of the evaluation unit 36 by appropriate parameters. The evaluation unit 36 thus detects whether the protected field is violated, i.e. whether an inadmissible object is within the protected field, and switches the safe output 38 depending on the result. In other embodiments, it is possible to do the evaluation or parts of the evaluation in a higher level control instead of in an internal evaluation unit 36.

All these functional components are arranged in a housing 40 which comprises a front screen 42 in the area where light enters and exits. This front screen 42 is curvedly formed so that light 44 reflected at the inside is focused in a focus area 46. In the situation of FIG. 1, a front screen reflection of the transmission light beam 16 is what is shown. However, the focusing also has an effect on other beam paths, for example on a beam path which is substantially reverse to the transmission light beam 16.

FIG. 2 shows a section of the front screen 42 in a direction perpendicular to the monitoring plane 22. The X-axis shows the diameter of the front screen 42 and the Y axis its height. The front screen 42 is a free-form surface whose contour in the section shown can be approximated by a polynomial or aspheric fit in virtually any desired accuracy. The particular curvature causes light 44a-c reflected at the inside of the front screen 42 to be focused in a common focus area 46 irrespective of the height position of the reflection. The focus area 46 is preferably arranged above, or in a mirrored arrangement below, the deflection unit 20. This is achieved by the contour of the front screen 42 as a whole being tilted outwardly or inwardly. Each secant 48 of the contour is therefore tilted with respect to a vertical line.

The front screen 42 is preferably curved over its entire height, wherein the curvature monotonically increases or decreases. The respective tilting of each infinitesimal front screen part thus decreases or increases accordingly so that with increasing distance to an upper or lower height level a larger deflection is caused. Various contours can be used, for example parabolic, hyperbolic, elliptic, or general aspheric curves.

The representations of FIGS. 1 and 2 each show a section perpendicular to the monitoring plane 22 at a fixed angular position of the deflection unit 20. In order to achieve the defined deflection of the front screen reflection 44 also in different angular positions, the front screen 42 is preferably designed as a body of revolution which has the required curvature in every angular position, i.e. in each perpendicular section to monitoring plane 22 including the rotational axis 20.

FIG. 3 shows a three-dimensional portion of such a front screen 42 formed as a body of revolution, some light beams 48a-e impinging in different heights and with different lateral offset, and corresponding reflected light 44a-e reflected at the inside of the front screen 42. The curvature of the front screen 42 has the effect in height direction and in circumferential direction that the reflected light 44a-e of the shown portion converges in a point or at least a very limited area. With additional angular positions, i.e. a larger angular section than illustrated, this results in a circumferential ring-shaped focus area 46 in a same height level. The front screen 42 as a three-dimensional body becomes bell-shaped or goblet-shaped.

FIG. 4 shows a three-dimensional view of the front screen 42 as well as other previously described elements of the sensor 10, namely, the light transmitter 12 with transmission optics 14, the light receiver 26 with reception optics 24, and the deflection unit 40. The representation of transmission optics 14 and reception optics 24 is simplified, other and more complex optical elements can also be used.

In order to test the light transmissivity of the front screen 42, a plurality of in this example six test light transmitters 50a-f are distributed in circumferential direction. One angular section, shown on the right in FIG. 4, is omitted as a dead zone of the scanning. In principle, sensors with a smaller or no dead zone are possible, where the test light transmitters 50a-f are distributed over a correspondingly larger angular section.

Reflectors 52a-f are associated with the test light transmitters 50a-f which are also distributed in circumferential direction in a plane parallel to the monitoring plane 22. These are preferably retroreflectors, because mirror elements, although in principle possible, would need to be precisely aligned, and diffusely scattering elements would lead to a substantially same beam path due to the curvature of the front screen 42, but would also cause stray light which is difficult to control. For a better understanding of the perspective of FIG. 4 it should be noted that the plane of the reflectors 52a-f is above the front screen 42. Contrary to the first impression, the reflectors 52a-f are thus arranged approximately symmetrically to the center axis.

The first test light transmitter 50a in an arbitrary counterclockwise numbering is aligned so that its test light impinges on the associated reflector 52a after passing through the front screen 42. The first test light path 54a then continues, after reflection at the reflector 52a with a partial reflection inside on both boundary surfaces of the front screen 42, to the deflection unit 20 and finally through reception optics 24 to a test light receiver 56a in a plane of the light receiver 26. A focusing occurs at the curved front screen 42 and at the reception optics 24. FIG. 4 shows only a main light path as test light path, adjacent light beams are guided correspondingly due to the described focusing properties. The deflection unit 20 faces the first test light transmitter 50a during the test by the first test light transmitter 50a. To ensure this, the activity of the test light transmitters 50a-f can be synchronized with the rotational movement of the deflection unit 20. Based on the signal of the test light receiver 56a, the evaluation unit 36 can evaluate the light transmissivity of the front screen 42 and, if necessary, output a maintenance signal or a safety related shutdown signal, respectively.

Preferably, optics which are not shown are arranged in front of the test light transmitters 50a-f, such as apertures or lenses, or light sources are used which already provide a collimated light beam. Optical elements, in particular lenses of these optics, can be formed integrally with a socket of the front screen 42, for example by injectionmolded lenses. Focusing the test light onto the reflector 52a-f is in particular useful for bright dust, because the measurement can be affected by stray light from the bright dust particles. Scattering from bright particles in particular affects the measurement if the energy part of the light beam impinging on the reflector 52a-f is low. By selection of optics and alignment of the test light transmitters 50a-f the position at which test light passes through the front screen 42 and the beam cross section can be optimally adjusted. The front screen 42 can also be irradiated with a larger area. The focussing properties due to the curvature of the front screen 42 and the reception optics 24 in the test light path 54a-f nevertheless provide a convergence onto the test light receiver 56a-b.

FIG. 5 shows the front screen 42 another time, now with the test light path 54c of the third test light transmitter 50c and associated reflector 52c. The deflection unit 20 has rotated and now faces the third test light transmitter 50c. The test light also on the third test light path 54c is guided into the same test light receiver 56a. An analog representation for the second test light path 54b starting from the second test light transmitter 54b is omitted because the situation is already understood from FIGS. 4 and 5. Thus, one common test light receiver 56a is sufficient for a plurality of test light paths 54a-c, in the shown example three test light paths 54a-c.

FIG. 6 shows the front screen 42 another time in a plan view for additional explanation. Focus area 46 is shown with a dashed line. Two auxiliary lines 58a-b show the possible circumferential positions of a radial offset with respect to the focus area 46. The reflectors 52a-c are arranged in the plane of the focus area 46 parallel to and above the monitoring plane 22 and distributed in circumferential direction. The positioning is done with a small offset with respect to a position marked with an x in the focus area 46. This position marked with an x is imaged centrally onto the light receiver 26.

Were one to arrange the reflectors 52a-c merely with an offset in a radial direction with respect to the position marked with an x, as shown by black dots, they would be imaged according to the arcuate arrangement in positions 60a-c at least partially next to and outside the test receiving element 56a. Therefore, the reflectors 52a-c get an additional angular offset with respect to the radial direction, as shown by arrows 60a-c. With a proper choice of the respective angular offset, the reflectors 52a-c, after Fresnel reflection at the inner and outer boundary surface of the front screen 42, are sharply imaged next to the light receiver 26 due to the curvature of the front screen 42 and the reception optics 24, and that at the same position within the plane of the light receiver 26, so that the test light reflected by the reflectors 52-c can be evaluated in the same test reception element 56a. The arrangement of the reflectors 52a-f should preferably be chosen such that also by the angular offset no reflector 52a-f is located in the focus area 46, because otherwise test light would reach the light receiver 26. If one wants to absorb the front screen reflection in an optical trap in the focus area 46, reflectors 52a-f could anyway not additionally be positioned in this area.

FIGS. 7 and 8 show a three-dimensional view of the front screen 42 corresponding to FIG. 4 with a fourth test light path 54d and a fifth test light path 54e. A corresponding representation for a sixth test light path 54f was omitted because its path is already understood from FIGS. 7 and 8. As on the first to third test light paths 54a-c, test light on the fourth to sixth test light paths 54d-f also reaches a common test light receiver 56b. The explanation, which would be based on a representation corresponding to FIG. 6 but vertically mirrored, is not repeated here.

Thus, for a light transmissivity measurement of the front screen at six positions with six test light paths 54a-f, only two test light receivers 56a-b are required. As the test light receivers 56a-b are close to each other in the same plane, they can be arranged on a common circuit board. This may even be the circuit board of light receiver 26 which is also on the same plane.

If distinguishable modulation properties or spectral properties are used for the transmission light beam 16 of the actual measurement of the sensor 10 and for the test light, the evaluation unit 36 can make a distinction so that test light scattered into the light receiver 26 does not interfere.

It is even possible to completely dispense with test light receivers 56a-b based on such distinguishable properties and to use light receiver 26 in a double function also for the transmissivity measurement of the front screen 42. To that end, in an embodiment, the reflectors 52a-f are arranged within the focus area 46 without an offset. Preferably, reflectors 52a-f are used which selectively reflect only the test light, because otherwise parts of the transmission light beam 16 could impinge on the light receiver 26 as interfering light.

FIGS. 9 and 10 again show the front screen 42 in a three-dimensional representation to explain reference light transmitters 62a and reference light paths 64a. Contamination of the front screen 42 is not the only possible cause for a change in the signal of the test light receivers 56a-b, but there are also other reasons like temperature effects, aging or similar effects. In order to compensate for these effects, the signal on the reference light paths 64a-b is determined which differ from the test light paths 54a-f in that they do not pass through the front screen 42. The reference light transmitters 62a-b are arranged above, below or inside the front screen 42. Although it is possible to use separate reference reflectors and reference light receivers, already existing reflectors 52c-d are used in the shown exemplary embodiments, and the reference light paths 64a-b lead to the test light receivers 56a-b by appropriate arrangement and orientation of the reference light transmitters 62a-b. This does not only have the advantage that components can be saved. In addition, effects of components actually used by the test light are compensated for, not merely of identical components as usually.

FIG. 11 shows in a sectional view the beam path of the transmission light beam 16 up to a front screen reflection. This beam path is essentially the reverse of a test light path 54a-f. The front screen reflex is measured in the focus area 46 with a fogging test receiver 66. To be precise, two light spots arise from the front screen reflection in the plane of the focus area 46 for each angle, namely, at the inner and outer boundary surface of the front screen 42. If the front screen 42 is covered by a liquid or other material from the outside, such as oil or water, as is the case for fogging, the resulting reflection at the outer boundary surface is attenuated due to the lower refractive index gradient. In this manner, a fogging can be detected from an evaluation of the front screen reflection at the outer boundary surface.

The invention claimed is:

1. An optoelectronic sensor (10) having a circumferential front screen (42) comprising a curvature both in a circumferential direction and in a height direction transverse to the circumferential direction and thus having a circumferential focus area (46) in which light reflected at the inside of the circumferential front screen (42) is focused, wherein a plurality of test light transmitters (50a-f) located on a first side of the front screen (42), at least one reflector (52a-f), and at least one test light receiver (56a-b) form a test light path (54a-f) on which test light passes from the test light transmitter (50a-f) through the front screen (42) to the reflector (52a-f) and subsequently onto the test light receiver (56a-b), and wherein an evaluation unit (36) is provided which is configured to detect a decreasing light transmissivity of the front screen (42) based on a decrease of a signal generated by the test light in the test light receiver (56a-b), characterized in that the test light receiver (56a-b) and the reflector (52a-f) are arranged on a second side of the front screen (42) opposing the first side of the front screen (42) such that the test light path (54a-f) leads from the reflector (52a-f) via a reflection on the inside of the front screen (42) to the test light receiver (56a-b), wherein the test light path (54a-f) of the plurality of test light transmitters (50a-f) share a common test light receiver (56a-b).

2. The sensor (10) according to claim 1, which is configured as a laser scanner comprising a light transmitter (12) for transmitting a transmission light beam (16) into a monitoring area (22), a light receiver (26) for generating a reception signal from a remitted light beam remitted from objects in the monitoring area (22) and a deflection unit (20) rotatable around a rotational axis for periodically deflecting the transmission light beam (16) in order to scan the monitoring area (22) in the course of the rotation, wherein the evaluation unit (36) is further configured to obtain information about objects in the monitoring area (22) from the reception signal.

3. The sensor (10) according to claim 2, wherein the monitoring area (22) is a monitoring plane.

4. The sensor (10) according to claim 2, wherein the test light receiver (56a-b) is arranged near the rotational axis and with its optical axis parallel thereto so that the test light path (54a-f) passes from the inside of the front screen (42) via the deflection unit (20) to the test light receiver (56a-b).

5. The sensor (10) according to claim 4, wherein the evaluation unit (36) is configured to activate the test light transmitter (50a-f) synchronized with the rotation.

6. The sensor (10) according to claim 2, wherein reception optics (24) are arranged in front of the light receiver (26), and wherein the reception optics (24) are also part of the test light path (54a-f) between deflection unit (20) and test light receiver (56a-b).

7. The sensor (10) according to claim 1, wherein the reflector (52a-f) is arranged near the focus area (46) of the front screen (42) with an offset to the focus area (46).

8. The sensor (10) according to claim 3, comprising a plurality of reflectors (52a-f) which are arranged in a circumferential distribution in a plane parallel to the monitoring plane (22), wherein each reflector (52a-f) has an offset to the focus area (46) and a differing angle offset relative to a radial direction to the focus area (46) so that the test light reflected by the plurality of reflectors (52a-f) is guided via the front screen (42) to a common test light receiver (56a-b).

9. The sensor (10) according to claim 1, wherein the test light transmitter (50a-f) comprises test light transmission optics, and wherein the test light transmission optics are integrally formed with a socket of the front screen (42).

10. The sensor (10) according to claim 9, wherein the test light transmission optics are formed by molding of lenses into the socket.

11. The sensor (10) according to claim 1, wherein a plurality of test light receivers (56a-b) are arranged on a same circuit board.

12. The sensor (10) according to claim 11, wherein the circuit board is a circuit board of the light receiver (26).

13. The sensor (10) according to claim 1, wherein the light transmitter (12) and the test light transmitters (50a-f) are configured to transmit light with distinguishable modulation properties or spectral properties.

14. The sensor (10) according to claim 1, wherein the reflector (52a-f) is selective for test light and is arranged in the focus area (46).

15. The sensor (10) according to claim 1, wherein the light receiver is also configured as a test light receiver (56a-b).

16. The sensor (10) according to claim 1, wherein at least one reference light transmitter (62a-b) is arranged so that its reference test light impinges on a corresponding reflector (52c-d) without transmitting the front screen (42).

17. The sensor (10) according to claim 1, wherein at least one fogging test receiver (66) is arranged in the focus area (46), and wherein the evaluation unit (36) is configured to detect a fogging of the front screen (42) from a decrease of a part of a transmission light beam (16) of the sensor (10) which is reflected into the fogging test receiver (66) by the front screen (42).

18. The sensor (10) according to claim 3, the sensor (10) being configured as a safety laser scanner with a safety output (38) by the evaluation unit (36) being configured to determine whether an object is present in a protected area within the monitoring plane (22) and to thereupon output a safety-related shut-down signal via the safety output (38).

19. A method for testing a light transmissivity of a circumferential front screen (42) of an optoelectronic sensor (10), wherein test light passes on a test light path (54a-f) from a plurality of test light transmitters (50a-f) through the front screen (42) to at least one corresponding reflector (52a-f) and subsequently onto a test light receiver (56a-b), and wherein a decreasing light transmissivity of the front screen (42) is detected from a decrease of a signal generated in the test light receiver (56a-b) by the test light,
   wherein the test light transmitters are located on a first side of the front screen (42),
   characterized in that the test light is partially reflected at an inside of the front screen (42) after reflection at the reflector (52a-f) and is at the same time focussed due to a curvature of the front screen (42) both in a circumferential direction and a height direction transverse to the circumferential direction, wherein the test light is subsequently detected in the test light receiver (56a-b), wherein the reflector (52a-f) and the test light receiver (56a-b) are located on a second side of the front screen (42) opposing the first side of the front screen (42),
   wherein the test light path (54a-f) of the plurality of test light transmitters (50a-f) share a common test light receiver (56a-b).

* * * * *